(12) United States Patent
Dahiwadkar et al.

(10) Patent No.: US 12,390,487 B2
(45) Date of Patent: Aug. 19, 2025

(54) ANTISEPTIC SKIN PREP COMPOSITION

(71) Applicant: Solventum Intellectual Properties Company, Maplewood, MN (US)

(72) Inventors: Avanti D. Dahiwadkar, Bangalore (IN); Matthew T. Scholz, Woodbury, MN (US)

(73) Assignee: Solventum Intellectual Properties Company, Maplewood, MN (US)

(*) Notice: Subject to any disclaimer, the term of this patent is extended or adjusted under 35 U.S.C. 154(b) by 872 days.

(21) Appl. No.: 17/601,144

(22) PCT Filed: Apr. 2, 2020

(86) PCT No.: PCT/IB2020/053173
§ 371 (c)(1),
(2) Date: Oct. 4, 2021

(87) PCT Pub. No.: WO2020/202077
PCT Pub. Date: Oct. 8, 2020

(65) Prior Publication Data
US 2022/0193119 A1    Jun. 23, 2022

(30) Foreign Application Priority Data

Apr. 5, 2019  (IN) .............................. 201941013830

(51) Int. Cl.
| | | |
|---|---|---|
| *A61K 31/785* | (2006.01) | |
| *A61K 9/00* | (2006.01) | |
| *A61K 31/14* | (2006.01) | |
| *A61K 31/155* | (2006.01) | |
| *A61K 31/444* | (2006.01) | |
| *A61K 47/10* | (2017.01) | |
| *A61K 47/22* | (2006.01) | |
| *A61K 47/32* | (2006.01) | |

(52) U.S. Cl.
CPC .......... *A61K 31/785* (2013.01); *A61K 9/0014* (2013.01); *A61K 31/14* (2013.01); *A61K 31/155* (2013.01); *A61K 31/444* (2013.01); *A61K 47/10* (2013.01); *A61K 47/22* (2013.01); *A61K 47/32* (2013.01)

(58) Field of Classification Search
CPC .... A61K 31/785; A61K 9/0014; A61K 31/14; A61K 31/155; A61K 31/444; A61K 47/10; A61K 47/22; A61K 47/32
See application file for complete search history.

(56) References Cited

U.S. PATENT DOCUMENTS

| | | | |
|---|---|---|---|
| 7,422,388 | B2 | 9/2008 | Tufts |
| 8,436,050 | B2 | 5/2013 | Modak |
| 9,821,066 | B2 | 11/2017 | Dokken |
| 2004/0116551 | A1* | 6/2004 | Terry .................. C09D 175/08 523/122 |
| 2007/0253909 | A1* | 11/2007 | Magallon ............. A61K 31/155 514/634 |
| 2007/0254854 | A1 | 11/2007 | Magallon |
| 2012/0237452 | A1 | 9/2012 | Colomer |
| 2014/0261454 | A1* | 9/2014 | Dokken ................. A61B 46/40 128/849 |
| 2016/0213001 | A1* | 7/2016 | Parthasarathy .......... A61K 8/40 |
| 2017/0014358 | A1 | 1/2017 | Tuffley |

FOREIGN PATENT DOCUMENTS

| | | |
|---|---|---|
| WO | WO 2006-029255 | 3/2006 |
| WO | WO 2009-068144 | 6/2009 |
| WO | WO 2013-074860 | 5/2013 |

OTHER PUBLICATIONS

Glycerol; https://www.google.com/search?q=glycerol+also+known+as; site accessed Jul. 2024 (Year: 2007).*
'N-Tert-Octylacrylamide', PubChem, create date Mar. 26, 2005 (Mar. 26, 2005) retrieved from the internet on Jun. 30, 2020 (Jun. 30, 2020) at <https //pubchem ncbj nlm nihgovycompound/N-Tert-Octylacrylamide>.
International Search report for PCT International Application No. PCT/IB2020/053173 mailed on Aug. 27, 2020, 4 pages.

* cited by examiner

*Primary Examiner* — Robert A Wax
*Assistant Examiner* — John W Lippert, III

(57) ABSTRACT

The disclosed antiseptic composition has improved stability, flow control and tinting ability is provided. The antiseptic composition comprises a cationic antiseptic, an anionic tinting agent, a polymer that serves as a stabilizer and preferably a viscosity builder, an alcohol-based solvent and optionally a plasticizer and viscosity builder.

20 Claims, 2 Drawing Sheets

ANTISEPTIC SKIN PREP COMPOSITION

CROSS REFERENCE TO RELATED APPLICATIONS

This application is a national stage filing under 35 U.S.C. 371 of PCT/IB2020/053173, filed Apr. 2, 2020, which claims the benefit of India Application No. 201941013830, filed Apr. 5, 2019, the disclosures of each of which re incorporated by reference herein in their entireties.

FIELD

An antiseptic composition with improved stability, flow control and tinting ability is disclosed.

BACKGROUND

Antiseptic solutions are applied to a patient's body prior to surgery or other medical procedures where there is a risk of infection. These solutions act instantly as well as provide persistent antimicrobial activity. Commonly employed antiseptic solutions are sometimes colored such that the solution becomes visible when applied on the skin. This is preferred to allow identification of prepped areas. However, coloring agents can make the solution unstable resulting in precipitate formation that is visible within a few days at room temperature.

The foregoing drawback has been commonly addressed by mixing the colorant into the antiseptic solution only before applying it to the skin. For example, in U.S. Pat. No. 7,422,388 a two-part system consisting of a foam impregnated with a dye and a separate container for the antiseptic solution without dye has been designed such that the dye and cationic antiseptic solution come in contact only at the time of prepping when the solution flows through the foam.

Other single systems have been stabilized using polymeric colorants formed by a polymerization reaction between a polymer component and a dye as described in WO 2013/074860. This procedure calls for polymerization reactions during manufacturing, which is complicated as opposed to simple mixing. It is desirable for the antiseptic composition to remain stable for as long as possible and possess a long shelf life.

U.S. Pat. No. 9,821,066 consist of acrylic based film forming polymers but have limited stability of up to 3 months at room temperature when aged in a sealed container impermeable to water and lower alkyl alcohols (C1-C4), as well as lack viscosity. Some have used cationic excipients in an aqueous medium (surfactants, quaternary ammonium compounds that form a micelle complex with the anionic dye in aqueous solutions) as described in WO 2009/068144 A1. In other work, cationic antiseptics are stabilized with anionic dyes using various concentrations of non-ionic surfactants in an aqueous system. Some work has been done to study the process of addition of water, dye, alcohol and chlorhexidine gluconate to arrive at a stable formulation. However, a stable formulation for the duration of the shelf life of a typical product could not be obtained with the process or compositions recommended.

In developing nations, prepping of skin is generally done using a gauze dipped in the antiseptic solution to paint the body. Due to the low viscosity and surface tension of alcohol solutions, there is wastage of solution in the form of dripping and pooling at the sides. Optimizing the viscosity of the prep for better flow control and to form a uniform layer can help reduce wastage.

PVP-I based skin preps are very commonly used but have a longer drying time and require multiple layers of prepping. A combination of 2% w/v chlorhexidine gluconate and 70% v/v isopropyl alcohol has both these advantages over PVP-I but lack the ability to tint. However, when an anionic dye is used as a tinting agent in a system consisting of a cationic antiseptic, the solution becomes unstable resulting in precipitate formation that is visible within a few days at room temperature. Hence these solutions are not tinting in nature or lack sufficient stability.

Accordingly, there is a need to develop a stable, viscous antiseptic solution with at least one anionic dye in sufficient quantity to be visible on the skin of the patient, having good flow control, improved stability while maintaining sufficient adhesion.

SUMMARY

In general, the disclosure features a composition for antiseptic solution having properties of improved stability, visibility, good flow control and adhesion. In an aspect, the present disclosure provides a composition comprising at least one cationic antiseptic agent, at least one anionic colorant, at least one polymer or copolymer, at least one $C_1$-$C_4$ lower alcohol-based solvent and optionally a plasticizer.

In an embodiment, the disclosure provides for an antiseptic composition, said composition utilizes a synergizing effect manifested by a combination consisting of chlorhexidine gluconate, an anionic dye and a polymer which is stable and enhances visibility on the skin while yielding good flow control in a hydro alcoholic system with more than 60% v/v of a lower alcohol. The composition demonstrates excellent stability, viscosity of about 1-100 cp for better flow control to reduce dripping during application using a gauze, sponge or applicator and dye in an appropriate quantity to tint the skin for better visibility.

In still another embodiment, the non-ionic, polar polymer prevents the precipitation of a complex between the cationic antiseptic and the anionic colorant, over a duration of up to 24 months at real time conditions.

In an embodiment, the present disclosure provides for a composition for an antiseptic solution comprising:
(a) about 0.1 to 2.5 wt. % of at least one cationic antiseptic;
(b) about 0.01 to 0.1 wt. % of at least one anionic colorant;
(c) about 0.1 to 10 wt. % of a non-ionic, polymer or copolymer with polar binding sites wherein the polar site has a nitrogen carrying a positive charge and an oxygen carrying a negative charge;
(d) at least 60% by weight of a lower alcohol-based solvent;
(e) optionally a plasticizer.

Further scope of applicability of the present invention will become apparent from the detailed description given hereinafter. However, it should be understood that the detailed description and specific examples, while indicating embodiments of the invention, are given by way of illustration only, because various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION

Figure 1:
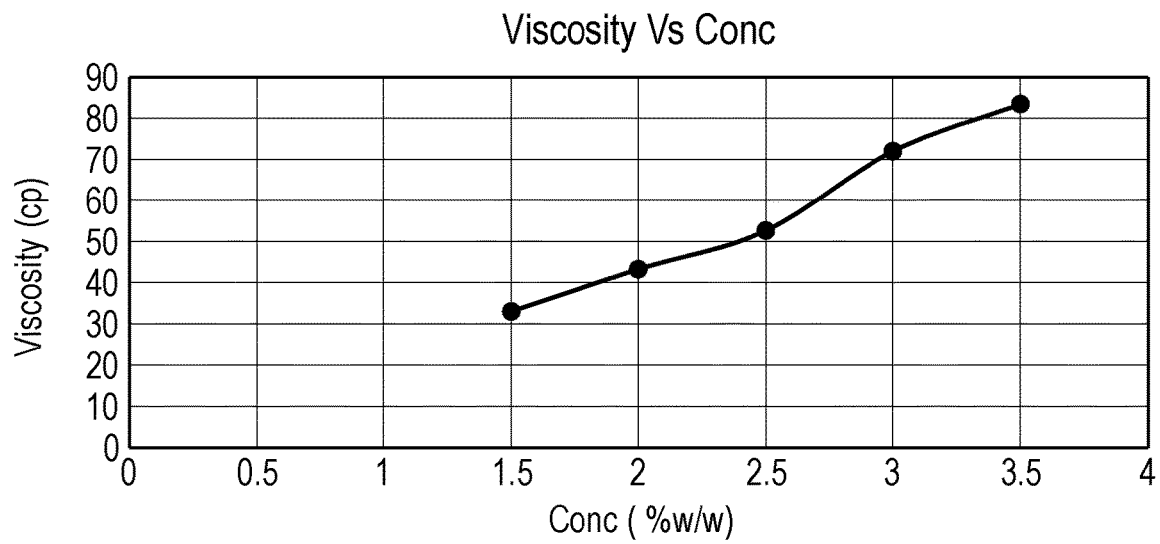
FIG. 1: Graph 1: Viscosity Vs Concentration (PVPK 120)

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for individual components, substituents, and ranges are for illustration only; they do not exclude other defined values or other values within defined ranges for the components and substituents.

As used herein, the singular forms "a," "an," and "the" include plural reference unless the context clearly dictates otherwise.

The use of numerical values in the various ranges specified in this application, unless expressly indicated otherwise, are stated as approximations as though the minimum and maximum values within the stated ranges were both preceded by the word "about". Thus, slight variations above and below the stated ranges can be used to achieve substantially the same results as values within the ranges. Moreover, in the disclosure of these ranges, a continuous range is intended, covering every value between the minimum and maximum values, including the minimum and maximum end points of the range.

As used herein, the term "disinfect", "disinfecting", "disinfection" shall mean the elimination of many or all microorganisms.

As used herein "antiseptic" refers to the ability of the composition to destroy microorganisms (e.g., skin flora, a bacterium, a fungus or virus), thereby rapidly disinfect the area applied on and prevent an infection or disease that may be caused.

As used herein, the term "stable" refers to the antiseptic composition which after 24 hours is clear and leaves no residue solid visible to the human eye. Moreover, the stable antiseptic solutions of the invention do not leave residue solids visible to the human eye after any standard stability test.

"Precipitation" here means the formation of any solids in the antiseptic composition of the present disclosure. Precipitation here means the particulate contamination that consists of extraneous, mobile, undissolved particles unintentionally present in the solution. Precipitation, particulate contamination can be measured by standard tests that are intended to provide a simple procedure for the visual assessment of the quality of the antiseptic solution.

According to one embodiment, an antiseptic skin prep solution comprises (a) a cationic antiseptic agent (b) at least one anionic colorant (c) a non-ionic, polymer or copolymer with polar binding sites wherein the polar site has a nitrogen carrying a positive charge and an oxygen carrying a negative charge (d) an $C_1$-$C_4$ lower alcohol based solvent (e) at least one plasticizer, wherein the non-ionic, polar polymer prevents or postpones the precipitation of the cationic antiseptic and the anionic colorant, over a duration of up to 24 months at 23 C. It is believed that this is achieved by formning a complex with the anionic colorant.

In one aspect of the invention, the antiseptic composition may comprise a cationic antiseptic agent. As used herein, a "cationic antiseptic" is any molecular entity having at least one positive charge and conferring an antimicrobial effect. The cationic moiety may be a quaternary amine or a protonated primary, secondary, or tertiary amine. As will be understood by one of skill, a given molecular entity may have properties of both a cationic excipient and an antiseptic. For example, the cationic antiseptic is selected from a group of chlorhexidine salts, PHMB salts, octenidine salts, alexidine salts, benzethonium salts, and combinations thereof.

According to one embodiment of the present disclosure, the cationic antiseptic provides a residual action and chlorohexidine digluconate (CHG) is employed in a representative composition.

CHG is an especially effective antiseptic as it exhibits a strong affinity for binding to skin, high antibacterial activity, and prolonged residual effects. It has been found that CHG is a broad range, rapid acting, and an excellent preoperative skin preparation. Further, CHG exhibits rapid activity against both gram-positive and gram-negative bacteria. Representative example of a CHG solution (Basic Pharma Life Science P Ltd.) is a 20% CHG.

The concentration of the cationic antiseptic is present in the range of 0.1-2.5% by weight of the composition.

The "dye" as described in the disclosure is alternatively referred to herein as a "colorant" or "tint". According to the present disclosure, the colorant is an anionic colorant. The anionic dye is any colorant that imparts a color to the antiseptic composition. According to one embodiment, the amount of anionic dye included in the composition is sufficient to be visible to the naked eye on a patient's skin when the composition is wet as well as once it is dried. One skilled in the art will appreciate that two or more anionic dyes may be combined and employed together.

An exemplary anionic dye is an FDA approved anionic dye added in sufficient concentration to tint the skin. Non-limiting examples of such exemplary anionic dyes include FD & C Red No. 3, FD&C Yellow No. 6, FD&C Blue No. 1, D&C Yellow 10, Brilliant Blue, D&C green, Carmoisine. Exemplary illustrated anionic dyes are Carmoisine, Erythrosine, Sunset yellow, Brilliant Blue, D&C Green.

In one embodiment, the total concentration of anionic dye will be from about 0.01-0.25% and preferably 0.015-0.1% by weight of the composition.

In one embodiment, the antiseptic skin prep composition comprises a polymer or copolymer. The polymer added is a high weight average molecular weight, non-ionic polymer with polar binding sites and a solubility parameter in the range of 18 to 28 (preferable around 24), such as polyvinyl pyrrolidone that builds viscosity in a hydro-alcoholic solution and prevents the formation of an insoluble precipitate of CHG-dye over a period of a minimum of 1 month to 24 months at 23 C in a sealed impermeable container. A solution of this nature has improved stability, viscosity of about (1-100 cp) for better flow control to reduce dripping during application using a gauze, sponge or applicator and dye in sufficient quantity to tint the skin for better visibility.

According to one embodiment, the concentration of dye to polymer in the antiseptic skin prep composition is in the ratio of 1:1 to 1:1000.

The following structure shows the charges on polyvinyl pyrrolidone and its affinity towards anionic species due to the positive charge on nitrogen. Without being bound to any theory, poly (vinyl pyrrolidone) is an electrolyte with an affinity for anionic species, enhancing the stability of the solution.

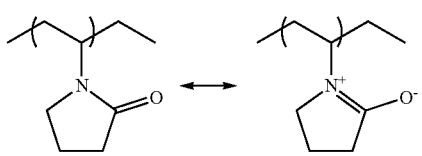

In an embodiment, the concentration of polymer will be from about 0.1 to 10 wt % by weight of the composition.

The non-ionic, polar polymer or copolymer is selected from a group consisting of poly (vinyl pyrrolidone), copolymers of PVP/VA, PVP/butene, polyamine oxides, polyethyloxazoline and/or combinations thereof where VA is vinyl acetate.

It is preferable that the polymer is a high weight-average molecular weight polymer greater than 100,000 g/mol, preferably greater than 300,000 g/mol, and more preferably 900,000-3000,000 g/mol.

According to an embodiment of the disclosure the polymer employed is PVPK 120.

The solvent includes an alcohol, preferably isopropyl alcohol, ethanol or n-propanol present in a concentration greater than 60% v/v. A plasticizer may be added to prevent cracking of the prepped film.

In an embodiment, the composition has a pH in the range of 5 to 7.5.

According to yet another embodiment, process of preparing an antiseptic skin prep composition comprises at least the following steps: of mixing until dissolution at least one anionic dye, cationic antiseptic and non-ionic, polymer or copolymer with polar binding sites wherein the polar site has a nitrogen carrying a positive charge and an oxygen carrying a negative charge with a molecular weight of at least 100,000 g/mol with a lower alcohol solvent and water wherein said components are present in the antiseptic solution in an amount sufficient to tint a patient's skin when applied thereto and wherein the non-ionic, polar polymer prevents or postpones the precipitation of a complex between the cationic antiseptic and the anionic colorant, over a duration of up to 24 months at real time conditions of 23 C.

All constituents employed in the final recommended composition are cosmetically and pharmaceutically acceptable with no significant toxicity. A high weight average molecular weight polyelectrolyte (polyvinyl pyrrolidone) provides the preferred viscosity and stability to a system with min 60% v/v of a lower alcohol (isopropyl alcohol/n-propanol/ethanol). 2% w/v chlorhexidine gluconate provides the residual activity and a FD&C dye as an anionic dye is present in sufficient quantity to tint skin of various shades.

According to the present disclosure, the viscosity of an exemplary composition is in the range of 1 to 100 cp.

Advantageously, the composition remains stable without any visible precipitate for up to 24 months at a temperature of 23-25 deg C. when sealed in an impermeable container such as glass or PET (Polyethylene terephthalate) that act as a barrier to alcohol and water evaporation.

The composition remains stable without any visible precipitate for up to 6 months at a temperature of 40 deg C. when sealed in an impermeable container.

An embodiment of the present invention is directed to a kit comprising, a cationic antiseptic agent and non-ionic polymer in solution separated from an anionic colorant, the components mixed just prior to use remain stable without precipitation for at least 5 mins, more preferably 30 mins, most preferably for an hour at 23 deg C.

The method of the present invention includes a method of disinfecting a surface comprising applying the antiseptic composition disclosed above to a surface. The surface can be human skin. The method may further include the steps of scrubbing the antiseptic on the skin, allowing the antiseptic composition to dry, and optionally apply an adhesive coated sheet commonly referred to as an incise drape over the dry antiseptic composition.

Illustrative example compositions which may be produced include those set forth below. The illustrative example compositions demonstrate certain particularly desired embodiments of the invention as well as preferred weight percentages as well as preferred relative weight percentages/weight ratios with regard to the respective individual constituents present within a composition.

EXAMPLE 1

Stability of Cationic Antiseptic and an Anionic Dye in a Hydro-Alcoholic System

An anionic dye, carmoisine, was added in sufficient quantity to tint the skin to a 2% CHG and 70% IPA (isopropyl alcohol) solution. The solutions were sealed in impermeable containers and allowed to sit at 23 C. At a pH where CHG is active a dark precipitate was observed in 5 days. Precipitation was accessed by shaking the sealed barrier container and visually looking for precipitate.

TABLE 1

| Cationic antiseptic and anionic dye without stabilizer | | | | | |
|---|---|---|---|---|---|
| Carmoisine | IPA | 20% CHG solution | Water | pH | Precipitation Day |
| 0.07 | 65.65 | 12.65 | 21.63 | 5.6 | 5 |
| 0.05 | 65.65 | 12.65 | 21.65 | >7 | 12 |

EXAMPLE 2

Comparative Test of Polymers for Solubility in a Hydro Alcoholic System, Thickening and Ability to Postpone Precipitation Polymers were tested for solubility, thickening and stabilizing effects. Various polymers were dissolved in an ethanol/isopropyl alcohol and water mixture. CHG and Carmoisine were added to the composition. The solutions were sealed in standard 100 ml TARSON PET containers of internal diameter 4.5 cm and allowed to sit at 23 C. The viscosity was measured, and homogeneity or stability was observed immediately and for 30 days.

TABLE 2

| | \multicolumn{10}{c}{Test of viscosity builder (All values are in w/w %)} | | | | | | | | | |
|---|---|---|---|---|---|---|---|---|---|---|
| | 1 | 2 | 3 | 4 | 5 | 6 | 7 | 8 | 9 | 10 |
| Water | 21.6 | 21.4 | 21 | 21.63 | 20.83 | 20.69 | 21.01 | 19.96 | 23.1 | 19.62 |
| IPA | 65.6 | 65.1 | 65.6 | 65.65 | 65.65 | | 65.65 | 65.65 | 62.52 | 65.65 |
| Ethanol | | | | | | 65.98 | | | | |
| PolyOX (WSR N-12K) | | | 0.6 | | | 0.6 | 0.06 | 0.06 | 0.6 | |
| PolyOX (WSR 205) | | | | | 0.8 | | | | | |
| CMC | | | | 0.6 | | | | | | |
| HEC | | 0.8 | | | | | | | | |
| PVPK 120 | | | | | | | | | | 2 |
| 20% CHG | 12.6 | 12.5 | 12.6 | | 12.65 | | 12.65 | 12.65 | 12.65 | 12.65 |
| Carmoisine | 0.05 | 0.05 | 0.05 | | 0.05 | | 0.05 | 0.05 | 0.05 | |
| OFX 190 | | | | | | | | | 1 | |
| Tween 80 | | | | | | | 1 | | | |
| Triton x100 | | | | | | | | 1 | | |
| HEDTA | | | | | | | 0.06 | 0.06 | 0.06 | |
| Viscosity (cp) | NA | NA | 38.7 | NA | 35.5 | 38 | | | 38 | 37.5 |
| Stability on Day 0 | Yes | No. Precipitation in 10 mins | Yes | No. Settle down in 30 mins | Yes | Yes | Yes | Yes | Yes | Yes |
| Homogenous on Day 30 @ RT | No. Dark precipitate observed on day 5 | NA | No. White precipitate observed in the first week and then dark precipitate | No | No. White precipitate observed in the first week and then dark precipitate | No | No. Dark precipitate formed after 2 weeks | No. Dark precipitate formed after 2 weeks | No. Dark precipitate formed | Yes |
| Solubility in IPA/water | Yes | No | Yes | No | Yes | NA | Yes | Yes | Yes | Yes |

IPA = Isopropyl alcohol from Deepak Fertilizers & Petrochemicals Corp. Ltd
Ethanol 95% = Sterling Chemicals & Alcohols Pvt. Ltd
20% CHG solution = Basic Pharma Life Science P Ltd.
POLYOX NF 12 = high molecular weight Poly ethylene oxide from Dow Chemical International Pvt. Ltd.
POLYOX WSR 205 = high molecular weight Poly ethylene oxide from Dow Chemical International Pvt. Ltd.
PVPK30 = Polyvinylpyrrolidone from Ashland
PVPK120 = high molecular weight Polyvinylpyrrolidone from Ashland
HEC = Hydroxyethyl cellulose, DOW Chemicals
CMC = Carboxymethyl cellulose from Sigma-Aldrich
Carmoisine = Acid Red 14 from Neelikon
OFX 190 = Dow Corning(I)Pvt Ltd
Tween 80 = Non-ionic surfactant and emulsifier from Sigma-Aldrich
Triton x100 = nonionic surfactant from Sigma-Aldrich Exp 1 as tabulated above shows that a solution without a viscosity builder or polymer has no significant viscosity and is not stable with visible precipitate in 5 days. Exp 3, 5, had a non-ionic polymer of ethylene oxide, POLYOX, of different molecular weights and concentrations. As the concentration increased there was a significant build up in viscosity of the solution. However, within a few days, a white precipitate began to settle at the bottom of the formulation followed by a dark precipitate later. Upon examination it was found that the interaction of CHG with calcium ions in POLYOX was causing the white precipitate. In Exp 7,8,9, HEDTA was used to scavenge the free Calcium resulting in no white precipitate, however the dark precipitate was still observed even when a non-ionic surfactant (Tween 80, Triton X-100) and OFX 190 (dimethicone copolymer) was added to stabilize the CHG-Dye interaction. POLYOX did postpone the interaction of dye and CHG but not sufficiently.

Other viscosity builders and film forming polymers were tried in Exp 2,4. HEC and CMC were insoluble in IPA/Water mixtures at the given ratio. HEC was soluble in Ethanol/Water mixture but separated out over time. PVPK 30 was soluble with good film forming but did not build any viscosity.

In Exp. 10, PVPK 120 was used and the best results were observed in terms of stability, viscosity build up and film forming. PVPK 120 is high molecular weight non-ionic, polymer with polar binding sites wherein the polar site has a nitrogen carrying a positive charge and an oxygen carrying a negative charge such that they interact with the anionic dye and cationic antiseptic to postpone precipitation.

Other polymers having similar structures were also studied for their stabilizing effect.

EXAMPLE 3

Non-ionic polymers or co-polymers having similar structures with polar groups having a positively charged nitrogen and negatively charged oxygen in a hydro-alcoholic solution in the presence of CHG and an anionic dye were also studied for their stabilizing effect. The solutions were sealed in standard 4 oz. glass jars of internal diameter 4.5 cm by Fisher Scientific, Pittsburgh PA and allowed to sit at 23 C for 17 days.

TABLE 3

Precipitation measurement of solutions with non-ionic polymers with nitrogen and oxygen when compared to a control having no polymer.

| | Control 1 | Z711 2 | Z712 3 | 2000 4 | 1-Step 5 | G904 6 | Gaf755 7 | E335 8 | Aqz500 9 |
|---|---|---|---|---|---|---|---|---|---|
| Sunset yellow (Yellow #6) dye | 0.02 | 0.02 | 0.02 | 0.02 | 0.02 | 0.02 | 0.02 | 0.02 | 0.02 |
| CHG 20% | 10 | 10 | 10 | 10 | 10 | 10 | 10 | 10 | 10 |
| Isopropanol | 70 | 70 | 70 | 70 | 70 | 70 | 70 | 70 | 70 |
| water | 17.98 | 17.48 | 17.48 | 16.65 | 15.98 | 17.98 | 11.98 | 17.98 | 18.98 |
| Diaformer Z711 40% in EtOH polyamine oxide | | 2.5 | | | | | | | |
| Diaformer Z712 40% in ETOH polyamine oxide | | | 2.5 | | | | | | |
| in EtOHRAM Resin 2000 poly(betaine) methacrylate 30% | | | | 3.33 | | | | | |
| 3M amine oxide polymer 25% in water | | | | | 4 | | | | |
| Ganex 904 VP/butene copolymer 100% | | | | | | 1 | | | |
| gafquat 755 VP/DMAEM copolymer | | | | | | | 1 | | |
| PVP/VA E335 30/70 50% | | | | | | | | 2 | |
| Aquazol 500 polyethyloxazoline 100% | | | | | | | | | 1 |
| Precipitation on a level of 0 to 5 on day 17 at room temperature (23 C.) | 2 | 0 | 0 | 0 | 0 | 1 | 7 | 0 | 0 |

Diaformer Z711 is an acrylates/lauryl acrylate/stearyl acrylate/ethylamine oxide methacrylate available from Clariant Corp. Personal Care Branch Mt. Holly NC Diaformer Z712 is an acrylates/lauryl acrylate/stearyl acrylate/ethylamine oxide methacrylate available from Clariant Corp. Personal Care Branch Mt. Holly NC 3M amine oxide polymer is a copolymer of stearylmethacrylate (10%)/isobutylmethacrylate(20%)/amine oxide of dimethylaminoethylmethacryltae (50%) and methylmethacrylate (20%) and was prepared similar to Example 90 of U.S. Pat. No. 7,323,163

Ganex 904 P is a butene/vinyl pyrrolidone copolymer available from Ashland

Gafquat 755 is a Vinyl pyrrolidone/dimethylaminoethylmethacrylate copolymer available from Ashland PVP/VA is a vinyl pyrrolidone/vinylacetate 30/70 copolymer available from Ashland Aquazol 500 is available from Polymer Chemistry Innovations, Inc., Tucson, AZ Exp 1 is the control with precipitation level of 2 observed on a scale of 0 to 5. Exp 2,3,4,5,6,8,9 are non-ionic polymers with nitrogen and oxygen that postpone the precipitation beyond 15 days. Exp 7, Gafquat used is a cationic polymer resulting in quick and heavy precipitation with dye.

Exp 5, is made with the 3M one step prep polymer is an amine oxide copolymer of stearyl methacrylate, isobutyl methacrylate, Dimethylaminoethylmethacrylate, methyl methacrylate

EXAMPLE 4

Viscosity Profile with Concentration and Measuring Drying Time

TABLE 4

Viscosity, drying time measurements and dripping observation with increase in PVPK120 concentration

|  | DiffPVP-1 | DiffPVP-2 | DiffPVP-3 | DiffPVP-4 | DiffPVP-5 |
|---|---|---|---|---|---|
| Water | 21.421 | 20.921 | 20.384 | 19.884 | 19.384 |
| IPA | 65.65 | 65.65 | 65.65 | 65.65 | 65.65 |
| Carmoisine | 0.05 | 0.05 | 0.05 | 0.05 | 0.05 |
| PVPK120 | 1.5 | 2 | 2.5 | 3 | 3.5 |
| 20% CHG solution | 11.12 | 11.12 | 11.12 | 11.12 | 11.12 |
| 10% Lactic Acid | 0.259 | 0.259 | 0.296 | 0.296 | 0.296 |
| Initial pH | 7.14 | 7.06 | 6.98 | 7.13 | 7.05 |
| Final pH | 6.18 | 6.14 | 6.15 | 6.22 | 6.27 |
| Viscosity (spindle LV-02 62, 200 RPM, 25 C) | 33 | 43.2 | 52.6 | 72 | 83.4 |
| Drying Time (min:sec) | 3:50 | 4:16 | 4:36 | 3:45 | 3:46 |
| Dripping | Slight | No | No | No | No |

Viscosity was measured at 25 C using a Brookfield DV2T viscometer available from Brookfield Engineering using spindle LV-02 (62). Graph 1 of FIG. 1 shows that the viscosity increases as the concentration increases. An area on the hands of a human subject below the elbow was prepped and observed for drying time and dripping for each concentration. There was minimal dripping observed for viscosities above approximately 40 cp corresponding to about 2% PVPK 120 concentration. The prepping was done using a soaked open cell polyurethane sponge. The drying times as PVPK 120 concentrations changed did not vary much and all dried in under 5 mins. Adding a plasticizer like glycerol ensured a uniform film without cracking was observed when prepping was done with a gauze as well as a polyurethane foam.

EXAMPLE 4

Comparative Test: Stability and Tinting of Various Dyes

Many dyes were tried in the formulation and their stability was observed over 30 days at room temperature(23 C). These were prepped on skin of light and dark tone and the tinting was observed.

TABLE 4

Prepping with different dyes

|  | Exp No: | | | |
|---|---|---|---|---|
|  | DiffDye-1 | DiffDye-2 | DiffDye-3 | DiffDye-4 |
| Water | 19.28 | 19.28 | 19.28 | 19.28 |
| IPA | 65.65 | 65.65 | 65.65 | 65.65 |
| Brilliant Blue | 0.05 | | | |
| Carmoisine | | 0.05 | | |
| Ponceau 4 R | | | 0.05 | |

TABLE 4-continued

Prepping with different dyes

|  | Exp No: | | | |
|---|---|---|---|---|
|  | DiffDye-1 | DiffDye-2 | DiffDye-3 | DiffDye-4 |
| D&C Green | | | | 0.05 |
| PVPK120 | 2 | 2 | 2 | 2 |
| CHG | 12.65 | 12.65 | 12.65 | 12.65 |
| Lactic Acid | 0.37 | 0.37 | 0.37 | 0.37 |

TABLE 4-continued

Prepping with different dyes

|  | Exp No: | | | |
|---|---|---|---|---|
|  | DiffDye-1 | DiffDye-2 | DiffDye-3 | DiffDye-4 |
| Stability day 0 | S | S | S | S |
| Stability day 15 | S | S | NS | S |
| Stability day 30 | S | S | NS | S |
| Tinting | Y | Y | Y | N |

S = Stable, NS = Not Stable, Y = Yes, N = No

It was observed that, Ponceau 4R Dye precipitated on the second day. The others (Brilliant Blue, D&C Green, Carmoisine) were stable over 30 days at room temperature with no precipitation observed. PVPK 120 postpones the precipitation of anionic dyes with CHG to various degrees. It was observed that the azo dye structure with 3 sulphonate groups precipitated out of solution quicker. Erythrosine dye demonstrates good solubility in alcohol systems potentially due to more hydrophobic nature as compared to azo dye sulphonates.

EXAMPLE 5

Erythrosine at different concentrations to tint the skin.

Figure 2:
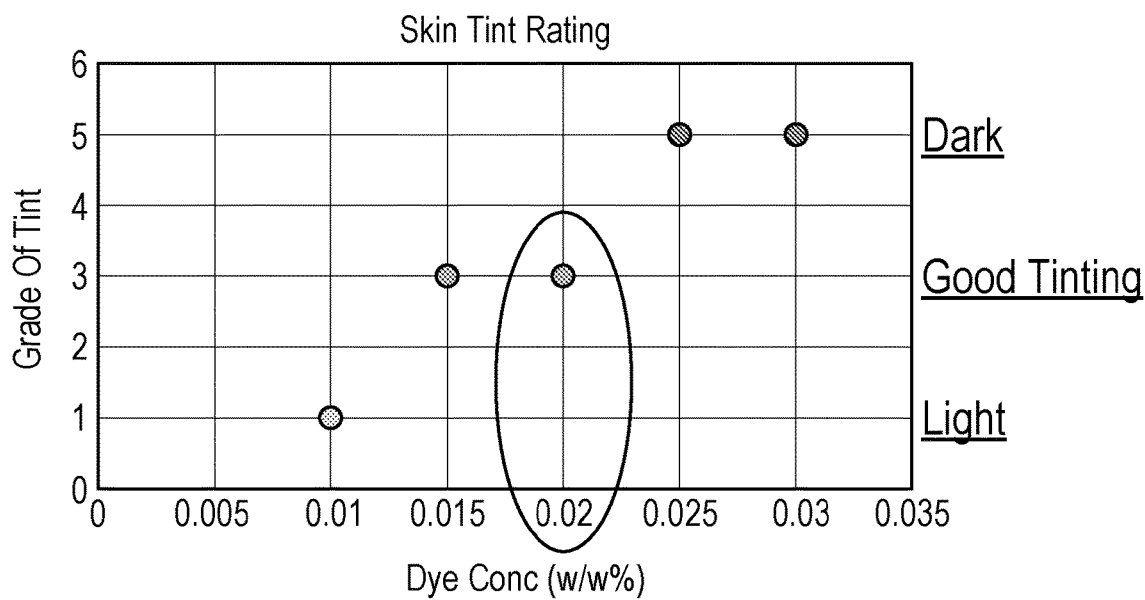
FIG. 2: Graph 2: Prepping of erythrosine at different dye concentrations
Figure 3:
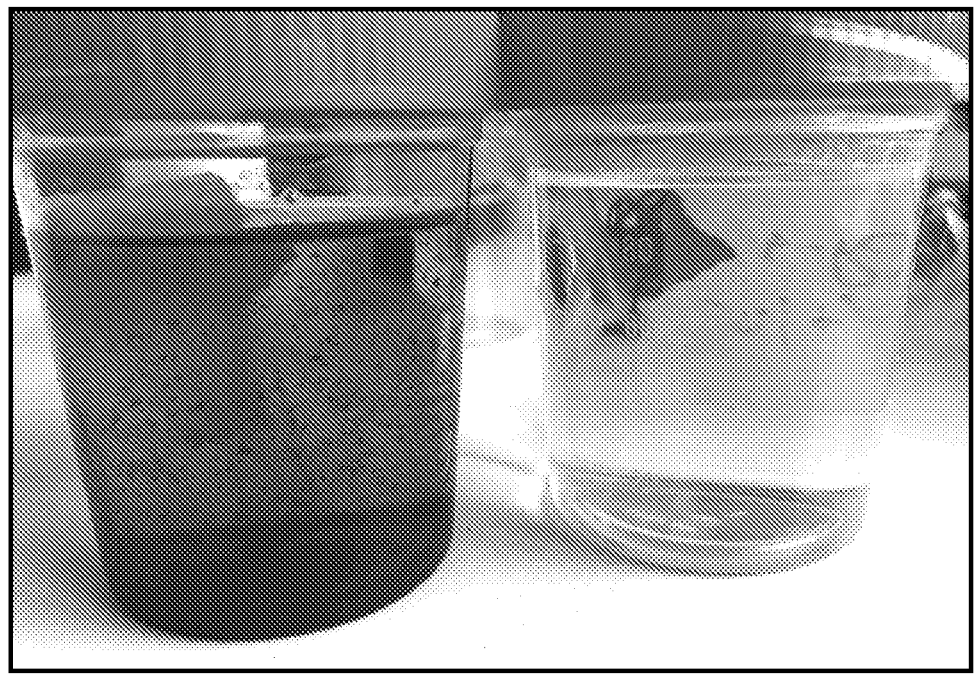
FIG. 3: Precipitate visible in an unstable solution with Ponceau 4 R dye (left) when compared to a stable solution with Quinoline Yellow dye (right)

In this example, tests were conducted to optimize the concentration of erythrosine at which the tinting is clear on skin of different tones (light, dark). Graph 2 (FIG. 2) depicts the prepping of erythrosine at different dye concentrations.

EXAMPLE 6

Stability Studies

Stability studies to observe for precipitation and other parameter was conducted under the following conditions sealed in an inert container impermeable to alcohol and water
1) 40 C for 6 months
2) 30 C for 24 months Sample made using erythrosine dye in sufficient quantity to tint the skin, 2% CHG, 70% IPA and 2.5% PVPK 120 and water qs.

TABLE 5

Real Time stability data of samples ED-29 and accelerated aging data of sample ED-30

| Stability condition | Experiment No: | Months | Appearance | CHG % w/v | pH | Viscosity |
|---|---|---|---|---|---|---|
| 23 C. | ED-9 | Initial | Pink with no precipitate | 2.0 | 5.8 | 52 |
|  | ED-9 | 24M | Pink with no precipitate | 1.9 | 6.0 | 53 |
| 30 C. | ED-30 | Initial | Pink with no precipitate | 2 | 5.8 | 60 |
|  | ED-30 | 24M | Pink with no precipitate | 2 | 6.1 | 55 |
| 40 C. | ED-29 | Initial | Pink with no precipitate | 2 | 5.8 | 60 |
|  | ED-29 | 6 | Pink with no precipitate | 2 | 6.4 | 60 |

The data shows that a solution with a cationic antiseptic (CHG) and anionic dye (erythrosine) remains stable upto 24 months at real time conditions and for a minimum of 6 months under accelerated aging conditions when a vinyl pyrrolidone polymer viscosity builder of high molecular weight is added. The enhanced viscosity also helps in flow control such that dripping of liquid is minimized.

The dye structure also impacts stability. Carmoisine which is an azo dye precipitated quicker (as seen in the table below) than erythrosine which is an organoiodide compound.

TABLE 6 pH and appearance, real time stability data and accelerated aging data of sample PT-3 using Carmoisine dye

| $6^{th}$ month ICH protocol | 6.73 | 3-5 particles |
| Real time - 3 months | 6.66 | No precipitate |
| Real time - 6 months | 6.69 | 1-2 particles |

While the invention has been described above with respect to certain embodiments thereof, numerous other forms and modifications will be apparent to those skilled in the art. The appended claims and the invention generally should be construed as covering all such obvious forms and modifications that are within the true spirit and scope of the invention.

It will thus be seen that the objects set forth above, among those made apparent from the preceding description are efficiently attained and since certain changes may be made in the above construction without departing from the scope of the invention, it is intended that all matter contained in the above description shall be interpreted as illustrative and not in a limiting sense.

We claim:

1. An antiseptic skin prep composition comprising:
   (a) cationic excipient consisting only of a cationic antiseptic agent;
   (b) anionic colorant;
   (c) a non-ionic polyvinyl pyrrolidone polymer or copolymer; and
   (d) $C_1$-$C_4$ alcohol-based solvent,
   wherein the antiseptic skin prep composition exhibits no visible precipitation when stored in a sealed inert barrier container having an internal diameter of 4.5 cm at 23 deg C. for at least 17 days.

2. The antiseptic skin prep composition as claimed in claim 1, wherein the cationic antiseptic agent is present in the range of 0.1-2.5% by weight of the antiseptic skin prep composition.

3. The antiseptic skin prep composition of claim 1, wherein the anionic colorant is present in the range of 0.01-0.1% by weight of the antiseptic skin prep composition.

4. The antiseptic skin prep composition of claim 1, wherein the non-ionic polyvinyl pyrrolidone polymer or copolymer is present in the range of 0.1 to 10% by weight of the antiseptic skin prep composition.

5. The antiseptic skin prep composition of claim 1, wherein the concentration of anionic colorant to non-ionic polyvinyl pyrrolidone polymer or copolymer is in the ratio 1:1 to 1:1000.

6. The antiseptic skin prep composition of claim 1, comprising at least 60% by weight of a lower alcohol.

7. The antiseptic skin prep composition of claim 1, wherein the cationic antiseptic agent is selected from a group of chlorhexidine salts, polyhexamethylene biguanide salts, octenidine salts, alexidine salts, benzethonium salts, and combinations thereof.

8. The antiseptic skin prep composition of claim 1, wherein the anionic colorant is selected from a group of anionic dyes including FD & C Red No. 3, FD&C Yellow No. 6, FD&C Blue No. 1, D&C Yellow 10, Brilliant Blue, D&C green and Carmoisine.

9. The antiseptic skin prep composition of claim 1, wherein the non-ionic polyvinyl pyrrolidone polymer or copolymer is selected from a group of polyvinyl pyrrolidone, copolymers of polyvinyl pyrrolidone and vinyl acetate, copolymer of polyvinyl pyrrolidone and butene, or combinations thereof.

10. The antiseptic skin prep composition of claim 1, wherein the non-ionic polyvinyl pyrrolidone polymer is polyvinyl pyrrolidone.

11. The antiseptic skin prep composition of claim 1, wherein the weight average molecular weight of the non-ionic polyvinyl pyrrolidone polymer or copolymer is 100,000-3,000,000 g/mol.

12. The antiseptic skin prep composition of claim 1, wherein the $C_1$-$C_4$ alcohol-based solvent is selected from a group of isopropyl alcohol, ethanol, n-propanol or combinations thereof.

13. An antiseptic skin prep solution of claim 1, characterized by a viscosity of 1 to 100 cp when measured using a Brookfield DV2T viscometer, spindle LV-02 at 23 C.

14. The antiseptic skin prep composition of claim 1, further comprising a plasticizer.

15. The antiseptic skin prep composition of claim 14, wherein the plasticizer is glycerol.

16. The antiseptic skin prep composition of claim 1, characterized as stable without any visible precipitate for at least 6 months at a temperature of 40 deg C.

17. A kit comprising:
an antiseptic skin prep composition of claim 1, and
gauze, foam, or prepping solution dispenser.

18. A kit comprising,
a cationic excipient consisting only of a cationic antiseptic agent and non-ionic polyvinyl pyrrolidone polymer or copolymer provided as a solution; and
an anionic colorant provided separate from the solution, wherein the solution and the anionic colorant are mixed just prior to use and remain stable without precipitation for at least 5 mins at 23 deg C.

19. A process of preparing an antiseptic skin prep composition of claim 1, the method comprising:
mixing until dissolved the following:
an anionic colorant;
a cationic antiseptic agent;
a non-ionic, polyvinyl pyrrolidone polymer or copolymer;
a $C_1$-$C_4$ alcohol; and
water.

20. The antiseptic skin prep composition of claim 1, wherein the non-ionic, polyvinyl pyrrolidone polymer or copolymer prevents or postpones precipitation of a complex between the cationic antiseptic agent and the anionic colorant for at least 17 days at 23 deg C.

* * * * *